(12) United States Patent
Shmidov et al.

(10) Patent No.: US 12,350,015 B2
(45) Date of Patent: Jul. 8, 2025

(54) RADIO FREQUENCY APPLICATOR

(71) Applicants: ENDRA Life Sciences Inc., Ann Arbor, MI (US); Duke University, Durham, NC (US)

(72) Inventors: Dima Shmidov, Durham, NC (US); Paolo Maccarini, Durham, NC (US); Idan Steinberg, Superior Charter Township, MI (US); Michael M. Thornton, London (CA); Christopher Nelson Davis, Ann Arbor, MI (US)

(73) Assignees: ENDRA Life Sciences Inc., Ann Arbor, MI (US); Duke University, Durham, NC (US)

( * ) Notice: Subject to any disclaimer, the term of this patent is extended or adjusted under 35 U.S.C. 154(b) by 147 days.

(21) Appl. No.: 18/506,722

(22) Filed: Nov. 10, 2023

(65) Prior Publication Data

US 2025/0152016 A1    May 15, 2025

(51) Int. Cl.
*A61B 5/00*    (2006.01)

(52) U.S. Cl.
CPC .......... *A61B 5/0093* (2013.01); *A61B 5/4244* (2013.01)

(58) Field of Classification Search
CPC .............................. A61B 5/0093; A61B 5/4244
See application file for complete search history.

(56) References Cited

U.S. PATENT DOCUMENTS

| | | |
|---|---|---|
| 10,682,059 B1 | 6/2020 | Davis et al. |
| 11,304,606 B2 | 4/2022 | Davis et al. |
| 11,337,676 B2 | 5/2022 | Barnes et al. |
| 11,369,272 B1 | 6/2022 | Davis et al. |
| 11,456,518 B2 * | 9/2022 | Davis .................... A61B 5/0095 |
| 11,619,613 B1 | 4/2023 | Davis et al. |
| 11,730,374 B1 | 8/2023 | Sengenberger et al. |

* cited by examiner

*Primary Examiner* — Peter Luong
(74) *Attorney, Agent, or Firm* — Stanley E. Jelic

(57) ABSTRACT

A radio frequency applicator, including a waveguide having a first interior surface comprising a first aperture, a second interior surface opposing the first interior surface, a third interior surface adjacent to the first and second interior surfaces, a fourth interior surface opposing the third interior surface, and a fifth interior surface perpendicular to the first, second, third, and fourth interior surfaces, an aperture antenna, a solid dielectric insert within the waveguide, the solid dielectric insert having a second aperture formed therethrough that is configured for alignment with the first aperture, an RF connector, configured to receive generated RF energy pulses, at least one planar-shaped shim, having a third aperture therethrough configured to align with the first and second apertures, and a radio frequency feed pin connected to the RF connector, disposed within the first, second, and third apertures and affixed to the second interior surface of the waveguide.

27 Claims, 5 Drawing Sheets

RADIO FREQUENCY APPLICATOR

TECHNICAL FIELD

This disclosure relates generally to radio frequency (RF) applicators, and more particularly to a RF applicators that are utilized to enable thermoacoustic measurements.

BACKGROUND

The statements in this section merely provide background information related to the present disclosure and may not constitute prior art.

In high frequency systems, it is common to employ waveguides to guide electromagnetic waves or sound with minimal loss of energy by restricting expansion of the electromagnetic waves propagating within the waveguides to one or two dimensions. Depending on the nature of the electromagnetic waves to be propagated, the waveguides may take different forms. In many instances, filters are employed to allow electromagnetic waves at some frequencies to pass and travel along the waveguides, while rejecting electromagnetic waves at other frequencies. For example, when propagating radio frequency (RF) waves, hollow, open-ended, conductive metal waveguides are often employed. In some instances, to provide the desired filtering, these hollow metal waveguides are fitted with a solid insert formed of high dielectric constant material.

Waveguides such as those described above have been employed in thermoacoustic imaging systems. Thermoacoustic imaging is an imaging modality that provides information relating to the thermoelastic properties of tissue. Thermoacoustic imaging uses short pulses of electromagnetic energy, such as RF pulses, directed into a subject to heat absorbing features within the subject rapidly, which in turn induces acoustic pressure waves that are detected using acoustic receivers such as one or more thermoacoustic or ultrasound transducer arrays. The detected acoustic pressure waves are analyzed through signal processing, and processed for presentation as thermoacoustic images that can be interpreted by an operator.

U.S. Pat. No. 10,682,059B1 to Davis et al. describes a waveguide with a solid insert and a wax to fill unwanted air pockets for thermoacoustic applications. For Davis, the feed distance in the waveguide is adjusted to optimize frequency. Unfortunately, the method and system cited in the Davis patent is difficult to tune to a desired frequency. Furthermore, the Davis method system suffers from fluctuations due to temperature changes, since the wax characteristics can change over time due to repeated heating and cooling cycles.

Further, the RF applicator structure described in Davis et al. is believed to have a capacitive effect. This is because the feed probe pin is not electrically connected to the aperture antenna. This makes it subject to material differences and temperature changes.

Hence, the current state of the art of waveguides for thermoacoustic applications has manufacturing, repeatability, and temperature drift problems, and therefore a need exists for improvement over the same, including embodiments of a waveguide having a non-capacitive effect configured to permeate a magnetic loop effect.

SUMMARY

A radio frequency (RF) applicator, including a waveguide having a first interior surface comprising a first aperture, a second interior surface opposing the first interior surface, a third interior surface adjacent to the first and second interior surfaces, a fourth interior surface opposing the third interior surface, and a fifth interior surface perpendicular to the first, second, third, and fourth interior surfaces, an aperture antenna, a solid dielectric insert within the waveguide, the solid dielectric insert having a second aperture formed therethrough that is configured for alignment with the first aperture, an RF connector, configured to receive generated RF energy pulses, at least one shim, wherein the at least one shim is planar-shaped and has a third aperture therethrough configured to align with the first and second apertures, and a radio frequency feed pin configured for electrical connection to the RF connector, wherein the radio frequency feed pin is disposed within the first, second, and third apertures and affixed to the second interior surface.

In one embodiment, the aperture antenna comprises an opening defined by the first, second, third, and fourth interior surfaces of the waveguide, wherein the opening is perpendicular to the first, second, third, and fourth interior surfaces and opposing the fifth interior surface.

In one embodiment, the RF applicator further comprises a conductive shim that is planar-shaped having a length corresponding to the fifth interior surface and the opening, and a width defined by the third and fourth interior surfaces and has a fourth aperture therethrough configured for alignment with the first and second apertures.

In one embodiment, the conductive shim has a conductivity between $1 \times 10^6$ Siemens/meter and $1 \times 10^8$ Siemens/meter.

In one embodiment, the RF applicator further comprises a compressible shim that is planar-shaped having a length corresponding to the fifth interior surface and the opening, and a width defined by the third and fourth interior surfaces and has a fourth aperture therethrough configured for alignment with the first and second apertures.

In one embodiment, the compressible shim has a bulk modulus between 1.0 Mega Pascal and 1.0 Giga Pascal.

In one embodiment, the compressible shim has an acoustic attenuation between 5 and 200 dB/(MHz*centimeter).

In one embodiment, the solid dielectric insert comprises a length corresponding to the fifth interior surface and the opening, and a width defined by the third and fourth interior surfaces.

In one embodiment, the solid dielectric insert has a real relative permittivity between about 20 and 180.

In one embodiment, the at least one shim is a dielectric shim.

In one embodiment, the at least one shim comprises a length corresponding to the fifth interior surface and the opening, and a width defined by the third and fourth interior surfaces.

In one embodiment, the at least one shim has a real relative permittivity between about 20 and 180 and an imaginary relative permittivity between about 0 and 18.

In one embodiment an RF applicator comprises: a waveguide having a first interior surface comprising a first aperture, a second interior surface opposing the first interior surface, a third interior surface adjacent to the first and second interior surfaces, a fourth interior surface opposing the third interior surface, and a fifth interior surface perpendicular to the first, second, third, and fourth interior surfaces; an aperture antenna; a solid dielectric insert within the waveguide, the solid dielectric insert having a second aperture formed therethrough that is configured for alignment with the first aperture; an RF connector, configured to receive generated RF energy pulses; a plurality of planar-shaped shims, each having an aperture therethrough configured to align with the first and second apertures; and a radio frequency feed pin configured for electrical connection to the RF connector, wherein the radio frequency feed pin is disposed within the first, second, and third apertures and affixed to the second interior surface.

In one embodiment, the plurality of planar-shaped shims comprises a conductive shim.

In one embodiment, the conductive shim has a conductivity between $1\times10^6$ Siemens/meter and $1\times10^8$ Siemens/meter.

In one embodiment, the plurality of planar-shaped shims comprises a compressible shim.

In one embodiment, the compressible shim has a bulk modulus between 1.0 Mega Pascal and 1.0 Giga Pascal.

In one embodiment, the compressible shim has an acoustic attenuation between 5 and 200 dB/(MHz*centimeter).

In one embodiment, the dielectric shim has a real relative permittivity between about 20 and 180 and an imaginary relative permittivity between about 0 and 18.

In one embodiment an RF applicator comprises: a waveguide having a first interior surface comprising a first aperture, a second interior surface opposing the first interior surface, a third interior surface adjacent to the first and second interior surfaces, a fourth interior surface opposing the third interior surface, and a fifth interior surface perpendicular to the first, second, third, and fourth interior surfaces; an aperture antenna; a solid dielectric insert within the waveguide, the solid dielectric insert having a second aperture formed therethrough that is configured for alignment with the first aperture; an RF connector, configured to receive generated RF energy pulses; a plurality of planar-shaped shims, each having an aperture therethrough configured to align with the first and second apertures, wherein the plurality of planar-shaped shims comprises: a conductive shim, a compressible shim, and at least one dielectric shim; and a radio frequency feed pin configured for electrical connection to the RF connector, wherein the radio frequency feed pin is disposed within the first, second, and third apertures and affixed to the second interior surface.

In one embodiment, the aperture antenna comprises an opening defined by the first, second, third, and fourth interior surfaces of the waveguide, wherein the opening is perpendicular to the first, second, third, and fourth interior surfaces and opposing the fifth interior surface.

In one embodiment, the conductive shim, the compressible shim, and the at least one dielectric shim, are planar-shaped having a length corresponding to the fifth interior surface and the opening, and a width defined by the third and fourth interior surfaces and each have an aperture therethrough configured for alignment with the first and second apertures.

This summary is provided merely to introduce certain concepts and not to identify key or essential features of the claimed subject matter.

BRIEF DESCRIPTION OF THE DRAWINGS

One or more embodiments will now be described, by way of example, with reference to the accompanying drawings, in which.

DETAILED DESCRIPTION

Figure 1:
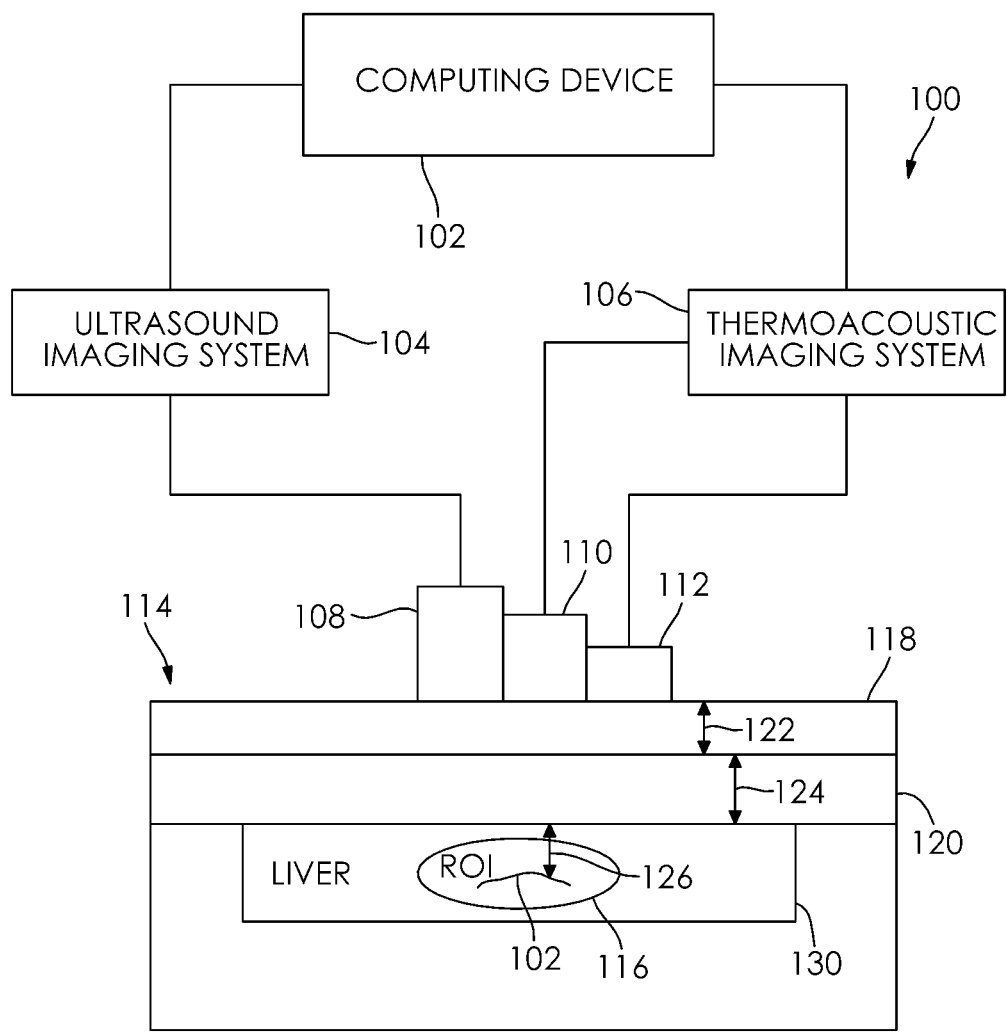
FIG. 1 schematically shows an exemplary imaging system and an exemplary region of interest in a liver with a blood vessel, in accordance with some embodiments.

Reference throughout this specification to "one embodiment," "an embodiment," or similar language means that a particular feature, structure, or characteristic described in connection with the embodiment is included in at least one embodiment of the subject matter of the present disclosure. Appearances of the phrases "in one embodiment," "in an embodiment," and similar language throughout this specification may, but do not necessarily, all refer to the same embodiment. The term "based upon" is not exclusive and allows for being based on additional factors not described, unless the context clearly dictates otherwise. Additionally, in the subject description, the word "exemplary" is used to mean serving as an example, instance or illustration.

Moreover, unless explicitly stated to the contrary, examples or embodiments "comprising" or "having" or "including" an element or feature or a plurality of elements or features having a particular property may include additional elements or features not having that property. Also, it will be appreciated that the terms "comprises", "has", "includes" means "including but not limited to" and the terms "comprising", "having" and "including" have equivalent meanings.

As used herein, the term "and/or" can include any and all combinations of one or more of the associated listed elements or features.

It will be understood that when an element or feature is referred to as being "on", "attached" to, "connected" to, "coupled" with, "contacting", etc. another element or feature, that element or feature can be directly on, attached to, connected to, coupled with or contacting the other element or feature or intervening elements may also be present. In contrast, when an element or feature is referred to as being, for example, "directly on", "directly attached" to, "directly connected" to, "directly coupled" with or "directly contacting" another element of feature, there are no intervening elements or features present.

It will be understood that spatially relative terms, such as "under", "below", "lower", "over", "above", "upper", "front", "back" and the like, may be used herein for ease of description to describe the relationship of an element or feature to another element or feature as illustrated in the figures. The spatially relative terms can however, encompass different orientations in use or operation in addition to the orientations depicted in the figures.

Reference herein to "example" means that one or more feature, structure, element, component, characteristic and/or operational step described in connection with the example is included in at least one embodiment and/or implementation of the subject matter according to the subject disclosure. Thus, the phrases "an example," "another example," and similar language throughout the subject disclosure may, but do not necessarily, refer to the same example. Further, the subject matter characterizing any one example may, but does not necessarily, include the subject matter characterizing any other example.

Reference herein to "configured" denotes an actual state of configuration that fundamentally ties the element or feature to the physical characteristics of the element or feature preceding the phrase "configured to".

Unless otherwise indicated, the terms "first," "second," etc. are used herein merely as labels, and are not intended to impose ordinal, positional, or hierarchical requirements on the items to which these terms refer. Moreover, reference to a "second" item does not require or preclude the existence of a lower-numbered item (e.g., a "first" item) and/or a higher-numbered item (e.g., a "third" item).

As used herein, the terms "approximately" and "about" represent an amount close to the stated amount that still performs the desired function or achieves the desired result. For example, the terms "approximately" and "about" may refer to an amount that is within engineering tolerances that would be readily appreciated by a person of ordinary skill in the art.

For the purposes of this disclosure, "aperture antenna" is defined as: a type of antenna that uses an opening or aperture in a conducting surface to radiate or receive electromagnetic waves. The aperture is typically a slot, a rectangular or circular opening, or a series of openings in a metal plate or other conducting surface. Aperture antennas are often used in applications where it is necessary to achieve high directivity or gain, such as in satellite communication, radar systems, and radio astronomy. They can also be used for imaging and sensing applications, such as in medical imaging and remote sensing. Aperture antennas are known for their high gain, low side-lobe levels, and narrow beamwidth, making them suitable for long-range communication and imaging applications. There are several types of aperture antennas, including: (1) Slot Antenna; A slot antenna is a type of aperture antenna that consists of a narrow slot cut into a conducting surface. The slot acts as an aperture, allowing electromagnetic waves to radiate or receive. (2) Horn Antenna; A horn antenna is a type of aperture antenna that consists of a flared metal horn that guides the electromagnetic waves. The horn can be rectangular or conical in shape, and it is typically fed with a waveguide or coaxial cable. (3) Microstrip Antenna; A microstrip antenna is a type of aperture antenna that consists of a thin, flat metal patch placed over a ground plane. The patch is typically rectangular or circular in shape, and it is fed with a coaxial cable or microstrip line.

Various embodiments of the present invention will be described in detail with reference to the drawings, where like reference numerals represent like parts and assemblies throughout the several views. Reference to various embodiments does not limit the scope of the invention, which is limited only by the scope of the claims attached hereto. Additionally, any examples set forth in this specification are not intended to be limiting and merely set forth some of the many possible embodiments for the claimed invention.

The RF applicator described in the present disclosure utilizes shims to tune to a desired frequency. The RF energy feed is in a fixed location and does not change position with temperature. Using multiple shims allows a coarse-tuning shim(s) to be combined with a fine-tuning shim(s) to achieve tight frequency tolerances for the RF applicator.

In some embodiments, a feed probe described herein is physically and electrically connected to an aperture antenna, so as to reduce or eliminate any capacitive effect. Instead of a capacitive effect, the potential for a magnetic loop effect exists in this embodiment.

Modeling and experimental results have shown that the magnetic loop effect of the RF applicator structure described in the present disclosure lowers reflected power and maximizes transmitted power.

In various embodiments, an optimal mathematical relationship (maximum transmitted power) between height (length of feed) and distance from the back wall (distance between feed and back wall that is opposite the waveguide opening) must be experimentally determined.

Referring now to the drawings, wherein the depictions are for the purpose of illustrating certain exemplary embodiments only and not for the purpose of limiting the same, FIG. 1 schematically shows an exemplary imaging system 100 is shown and is generally identified by reference numeral 100. As can be seen, the imaging system 100 includes a programmed computing device 102 communicatively coupled to an ultrasound imaging system 104 and to a thermoacoustic imaging system 106. The ultrasound imaging system 104 and thermoacoustic imaging system 106 are configured to obtain ultrasound image data and thermoacoustic image data, respectively, of a region of interest 116. Components of the system 100 are shown in FIG. 1 as single elements. Such illustration is for ease of description, and it should be recognized that the system 100 may include multiple additional imaging devices or sub-devices.

The programmed computing device 102 may be a computer, server or other suitable processing device comprising, for example, a processing unit comprising one or more processors, computer-readable system memory (volatile and/or non-volatile memory), other non-removable or removable computer-readable memory (e.g., a hard disk drive, RAM, ROM, EEPROM, CD-ROM, DVD, flash memory, etc.) and a system bus coupling the various computer components to the processing unit. The computing device 102 may also comprise networking capabilities using Ethernet, Wi-Fi, and/or other suitable network format, to enable connection to shared or remote drives, one or more networked computers, or other networked devices. One or more input devices, such as a mouse and a keyboard (not shown) are coupled to the computing device 102 for receiving operator input. A display device (not shown), such as one or more computer screens or monitors, is coupled to the computing device 102 for displaying one or more generated images that are based on ultrasound image data received from the ultrasound imaging system 104 and/or the thermoacoustic image data received from thermoacoustic imaging system 106. The programmed computing device 102 executes program code stored on the computer-readable system memory and/or other non-removable or removable computer-readable memory and performs methods according to the program code as will be described further below.

The ultrasound imaging system 104 comprises an acoustic receiver in the form of an ultrasound transducer 108 that houses one or more ultrasound transducer arrays configured to emit sound waves into the region of interest 116. Sound waves directed into the region of interest 116 echo off materials within the region of interest ROI, with different materials reflecting varying degrees of sound. Echoes that are received by the one or more ultrasound transducer arrays of the ultrasound transducer 108 may be processed by the ultrasound imaging system 104 before being communicated as ultrasound image data to the computing device 102 for further processing and for presentation on the display device as ultrasound images that can be interpreted by an operator. In one embodiment, the ultrasound imaging system 104 utilizes B-mode ultrasound imaging techniques assuming a nominal speed of sound of 1,540 m/s. As ultrasound imaging systems are known in the art, further specifics of the ultrasound imaging system 104 will not be described further herein.

The thermoacoustic imaging system 106 comprises an acoustic receiver in the form of a thermoacoustic transducer 110. The thermoacoustic transducer 110 houses one or more thermoacoustic transducer arrays. Radio-frequency (RF) applicator 112 may be housed together or separately from the thermoacoustic transducer 110. The RF applicator 112 is configured to emit short pulses of RF energy that are directed into the region of interest ROI, which contains blood vessel 128. In one embodiment, the RF applicator 112 has a frequency between about 10 Mhz and 100 GHz and has a pulse duration between about 0.1 nanoseconds and 10 microseconds. RF energy pulses delivered to materials within the region of interest 116 induce acoustic pressure waves (thermoacoustic multi-polar signals) within the region of interest 116 that are detected by the thermoacoustic transducer 110. Acoustic pressure waves that are detected by the thermoacoustic transducer 110 are processed and communicated as thermoacoustic image data to the computing device 102 for further processing and for presentation on the display device as thermoacoustic images that can be interpreted by the operator.

The coordinate system of the one or more ultrasound transducer arrays of the ultrasound transducer 108 and the coordinate system of the one or more thermoacoustic transducer arrays of the thermoacoustic transducer 110 are mapped by the computing device 102 so that acquired ultrasound and thermoacoustic images can be registered. Alternatively, the thermoacoustic imaging system 106 may make use of the one or more ultrasound transducer arrays of the ultrasound transducer 108 by disconnecting the one or more ultrasound transducer arrays from the ultrasound transducer 108 and connecting the one or more ultrasound transducer arrays to the thermoacoustic transducer 110. As will be appreciated, by doing this coordinate mapping between the one or more ultrasound transducer arrays and the one or more thermoacoustic transducer arrays is not required.

In one embodiment (shown in FIG. 1), an exemplary region of interest 116 contains a blood vessel 128 and is located within a liver 130 of a human or animal body (patient) 114. Patient 114 comprises a skin layer 202 and subcutaneous fat layer 204 and muscle layer 220 adjacent to liver 230.

Figure 2A:
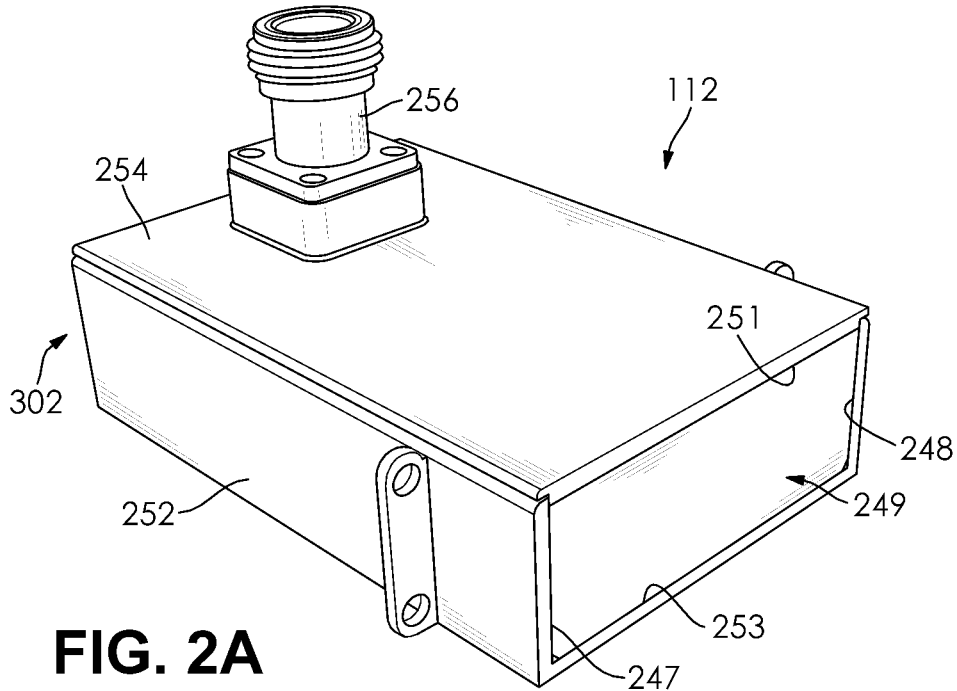
FIG. 2A shows a perspective view an exemplary RF applicator without shims or solid dielectric insert, in accordance with some embodiments.

FIG. 2A shows a perspective view of an exemplary RF applicator 112, which includes a waveguide 250. The applicator 112 includes RF connector 256 for selectively supplying generated RF energy pulses to the waveguide 250. In one embodiment, the waveguide 250 is formed of a base 252, a lid 254, and a back plate 302. In one embodiment, the waveguide 250 may be integrally formed, or formed of any number of components such that an opening 249 is formed on one end opposite the back plate 302. In one embodiment, the opening 249 functions as an aperture antenna. The opening 249 is perpendicular to a first and the second interior surfaces 251 and 253, respectively, of the waveguide 250.

Figure 2B:
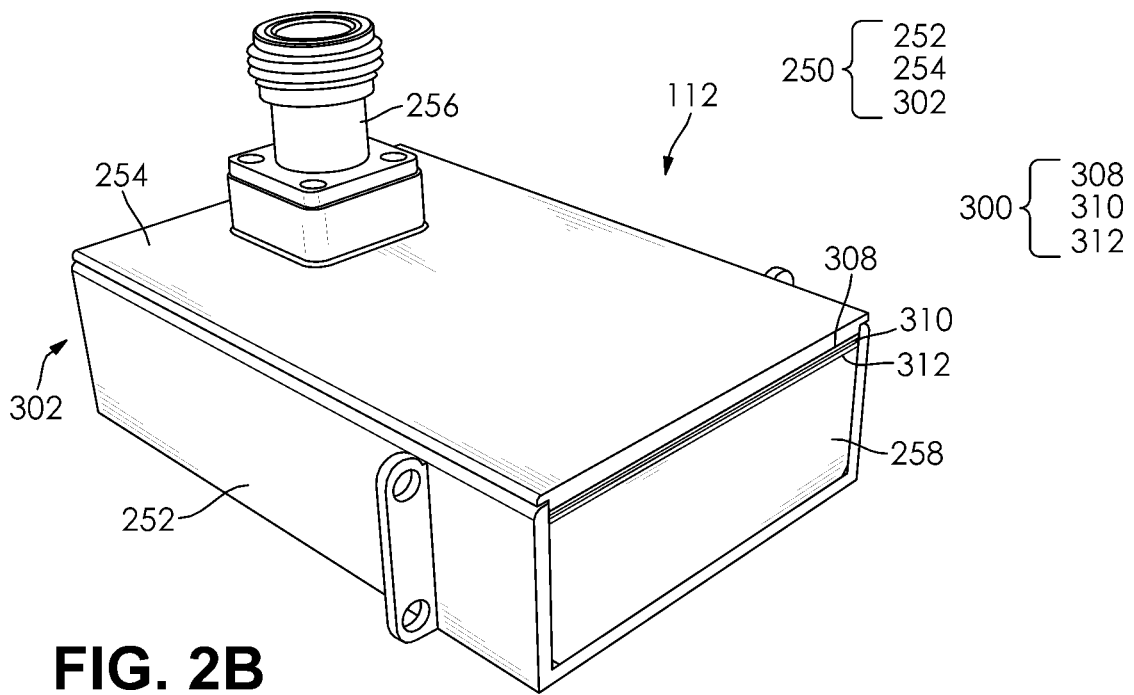
FIG. 2B shows a perspective view an exemplary RF applicator, in accordance with some embodiments.

FIG. 2B shows a perspective view of an exemplary RF applicator 112, which includes a waveguide 250. As FIG. 2B shows, the waveguide 250 includes the solid dielectric insert 258 which in one embodiment is a high permittivity block, compressible shim 308 which in one embodiment is a foam pad, conductive shim 310 which in one embodiment has a copper material of construction, and a first dielectric shim 312 which has a dielectric value chosen to enable coarse frequency tuning of RF applicator 112.

Figure 3A:
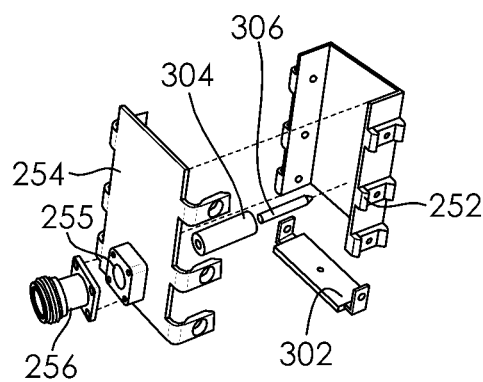
FIG. 3A shows an exploded view of an exemplary RF applicator, in accordance with some embodiments.
Figure 3B:
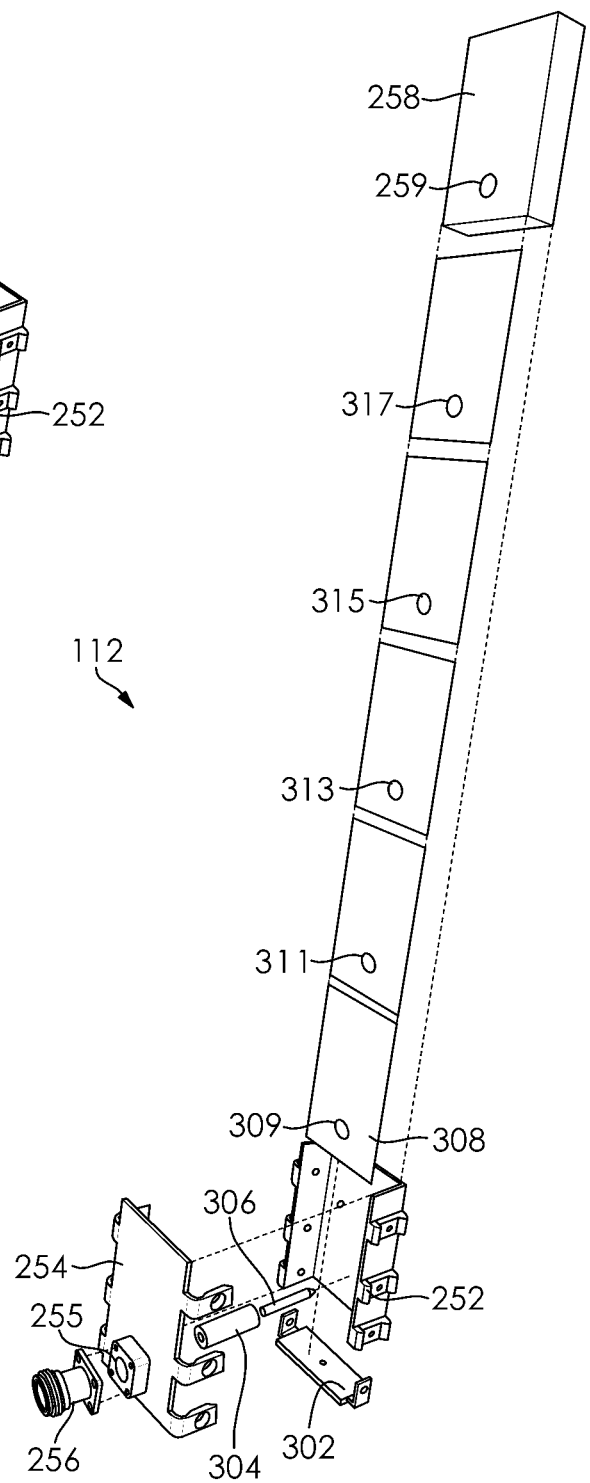
FIG. 3B shows an exploded view of an exemplary arrangement of shims within a waveguide of an exemplary RF applicator, in accordance with some embodiments.

FIGS. 3A and 3B show an exploded view of an exemplary RF applicator 112. As FIG. 3A shows, the RF applicator 112, includes a base 252, a lid 254, a RF connector 256, and a solid dielectric insert 258, which in one embodiment is a high permittivity block, a back plate 302, a dielectric insulator 304, and a feed probe pin 306. The lid 254 includes an aperture 255 therethrough.

In one embodiment, solid dielectric insert 258 has a real relative permittivity between about 20 and 180 and an imaginary relative permittivity between about 0 and 18.

In one embodiment, solid dielectric insert 258 has a dielectric constant between 55 and 65, or more preferably between 57 and 63.

The RF applicator 112 can include one or more shims 300. As FIG. 3 shows, the exemplary RF applicator 112 can include a compressible shim 308, which in one embodiment is a foam pad, a conductive shim 310, which in one embodiment has a copper material of construction, and one or more dielectric shims. As FIG. 3 shows, the RF applicator 112 can include a first dielectric shim 312 which has a dielectric value chosen to enable coarse frequency tuning of RF applicator 112, a second dielectric shim 314 which has a dielectric value chosen to enable fine frequency tuning of RF applicator 112, and a third dielectric shim 316 which has a dielectric value chosen to enable very fine frequency tuning of RF applicator 112.

In one embodiment, first dielectric shim 312 has a dielectric constant between 5 and 30, second dielectric shim 314 has a dielectric constant between 2 and 20, and third dielectric shim 316 has a dielectric constant between 1.5 and 15. These exemplary embodiments are meant to be non-limiting. For example, an embodiment could use three shims with dielectric constants that are all in the same range.

In one embodiment, the dielectric shims comprise an elastomer.

In one embodiment, the compressible shim 308 has a bulk modulus between 1.0 Mega Pascal and 1.0 Giga Pascal, or more preferably between 2 Mega Pascal and 0.8 Giga pascal.

In one embodiment, the compressible shim 308 has an acoustic attenuation between 5 and 200 dB/(MHz*centimeter). In a preferable embodiment, the acoustic attenuation of compressible shim 308 is between 6 and 150 dB/(MHz*centimeter).

In one embodiment, the conductive shim 310 functions as a grounding shim. In one embodiment, the conductive shim 310 has a conductivity between $1 \times 10^6$ Siemens/meter and $1 \times 10^8$ Siemens/meter.

In one embodiment, the dielectric insulator 304 is sized and shaped to receive the feed probe pin 306. In one embodiment, the dielectric insulator 304 is cylindrical in shape with a cylindrical-shaped void for receiving the feed probe pin 306. In one embodiment, the dielectric insulator 304 may be formed of most any non-metallic material configured to insulate electrical flow of the feed probe pin 306.

A first end 305 of the feed probe pin 306 is electrically connected to the RF connector 256. A second, opposing end 307, is affixed to the second interior surface of the waveguide 250, which in one embodiment is a bottom interior surface of the base 252. The feed probe pin 306 is disposed through apertures of the shims 300 and the solid dielectric insert 258.

FIG. 3B shows an exploded view of the shims 300 and the solid dielectric insert 258. As FIG. 3B shows, the shims 300 can include the compressible shim 308, the conductive shim 310, and the first, second, and third dielectric shims 312, 314, and 316, respectively. In one embodiment, the shims 300 may be arranged from a top surface 251 of the waveguide 250 to a bottom surface 253 in the order shown in FIG. 3B. In one embodiment, the order of the shims 300 and the solid dielectric insert 258 may be any order.

As FIG. 3B shows, each of the shims 300 and the solid dielectric insert 258 include an aperture. The compressible shim 308 includes aperture 309. The conductive shim 310 includes an aperture 311. The first dielectric shim 312 includes an aperture 313. The second dielectric shim 314 includes an aperture 315. The third dielectric shim 316 includes an aperture 317. The apertures 309, 311, 313, 315, 317, and 259 are preferably substantially sized and shaped for vertical alignment to receive an elongated cylindrical-shaped dielectric insulator. In one embodiment, the apertures 309, 311, 313, 315, 317, and 259 have an elliptical-shaped cross-sectional shape. In one embodiment, the apertures 309, 311, 313, 315, 317, and 259 have a circular-shaped cross-sectional shape.

In one embodiment, the shims 300 (e.g., the compressible shim 308, the conductive shim 310, the first, second, and third dielectric shims 312, 314, and 316) are planar-shaped and have a length corresponding to a length from an interior surface of the back plate 302 to the opening 249, and a width corresponding to a length from a first side interior planar surface 247 of the base 252 to a second interior planar surface 248 of the base 252. The solid dielectric insert 258, in one embodiment, has a length and width substantially similar to the shims 300.

Figure 4:
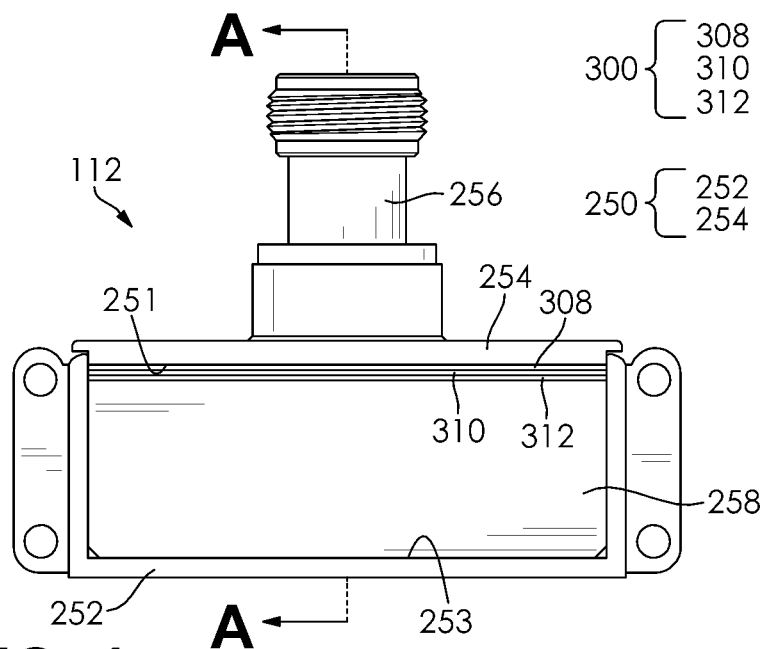
FIG. 4 shows a front view an exemplary RF applicator, in accordance with some embodiments.

FIG. 4 shows a front view of an exemplary RF applicator 112 including the waveguide 250. As FIG. 4 shows, the RF applicator 112 includes the base 252, the lid 254, the RF connector 256, the solid dielectric insert 258 and a plurality of shims 300. A top surface 251 of the waveguide 250 may be the bottom interior surface of the lid 254, in one embodiment. A bottom surface 235 of the waveguide 250 may be a top interior surface of a base 252, in one embodiment. The shims 300 include, the compressible shim 308, the conductive shim 310, and a first dielectric shim 312 which has a dielectric value chosen to enable coarse frequency tuning of RF applicator 112.

Figure 5:
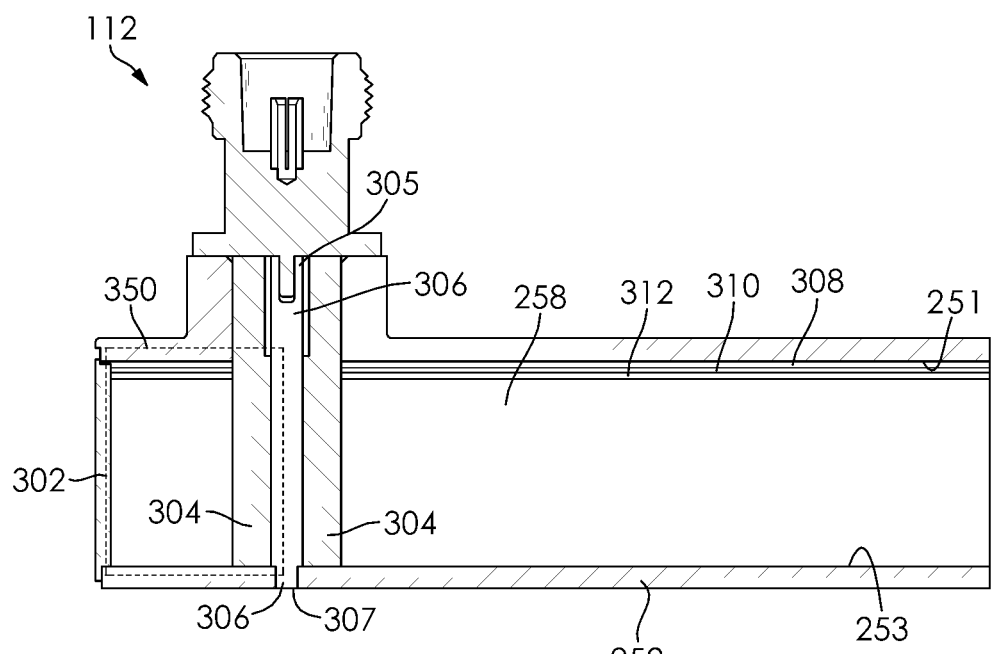
FIG. 5 shows a cross-sectional view of an exemplary RF applicator, viewed along line A-A of FIG. 4, in accordance with some embodiments.

FIG. 5 shows a side cross-sectional view of an exemplary RF applicator 112 with a waveguide 250. The waveguide 250 includes the base 252, the lid 254, and the back plate 302. The applicator 112 includes the waveguide 250, RF connector 256, solid dielectric insert 258, and a plurality of shims 300, the dielectric insulator 304, and the feed probe pin 306.

As FIG. 5 shows, the first end 305 of the feed probe pin 306 is electrically connected to the RF connector 256. A second, opposing end 307, is affixed to the second interior surface of the waveguide 250, which in one embodiment is a bottom interior surface 253 of the base 252. In one embodiment, the base 252 includes a mating indentation configured to receive or couple to the opposing end 307. The feed probe pin 306 is disposed through apertures of the shims 300 and the solid dielectric insert 258.

In operation, electric energy communicated to the RF applicator 112 via the RF connector 256 flows through the radio frequency feed pin 306. The dielectric insulator 304 inhibits electric energy outflow through sides of the radio frequency feed pin 306. The size and shape of the pin 306 generate a magnetic field having at least one defined magnetic loop, such as the exemplary magnetic loop 350 shown in FIG. 5.

Hence, the current state of the art of waveguides for thermoacoustic applications has manufacturing, repeatability, and temperature drift problems, and therefore a need exists for improvement over the same, including embodiments of a waveguide having a non-capacitive effect configured to permeate a magnetic loop effect.

Figure 6:
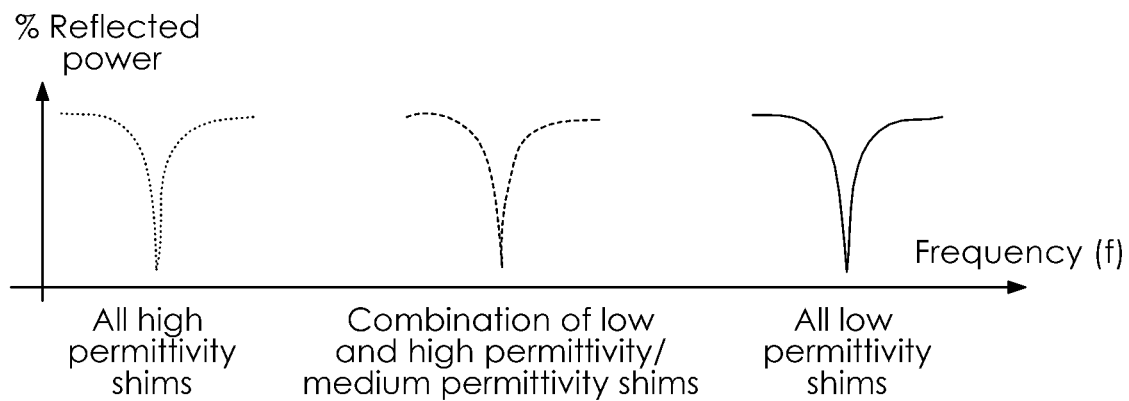
FIG. 6 shows that the resonance frequency of the RF applicator can be adjusted by changing the permittivity combination of the shims, in accordance with some embodiments.

FIG. 6 graphically shows that the resonance frequency of the RF applicator 112 can be adjusted by changing the permittivity combination of the shims 300, which can be achieved by selecting shims for inclusion in the waveguide 250. All high permittivity shims will give the lowest resonance frequency, all low permittivity shims will give the highest frequency, and a combination of permittivity shims between the high and low values will give a resonance frequency between these two frequencies.

In one embodiment, the target resonance frequency of RF applicator 112 is 434 MHz. Initially during construction, RF applicator 112 comprises solid dielectric insert 258 and an air gap, which results in a resonance frequency higher than the target resonance frequency of 434 MHz. Since air has low permittivity, replacing the air gap with shims will lower the resonance frequency of RF applicator 112. Adding the correct combination of shims 300 to displace the air gap will result in RF applicator 112 having a resonance frequency of 434 MHz. The same series of steps can be used to target other desired resonance frequencies for the RF applicator 112 (such as, but not limited to, 915 MHz).

Figure 7:
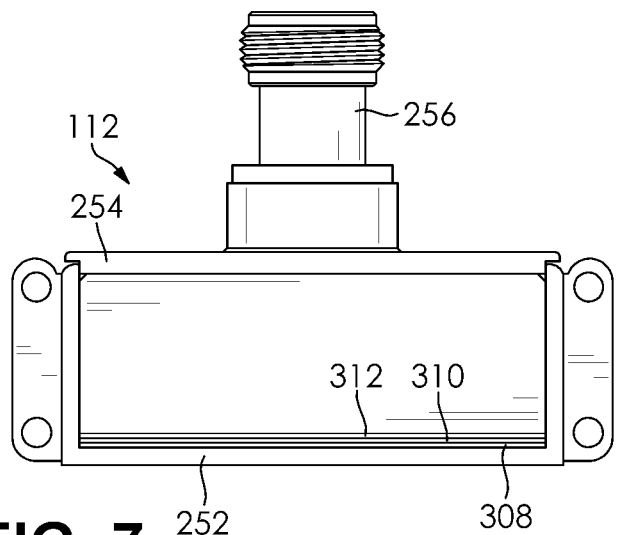
FIG. 7 shows a front view of an exemplary RF applicator with shims in an alternate location, in accordance with some embodiments.

FIG. 7 shows a front view of an exemplary RF applicator 112 with shims 300 disposed in an alternate arrangement within the waveguide 250. As FIG. 7 shows, the compressible shim 308, the conductive shim 310, and the first dielectric shim 312 may be disposed below the solid dielectric insert 258. In another embodiment, one or more additional dielectric shims are disposed therein.

Figure 8:
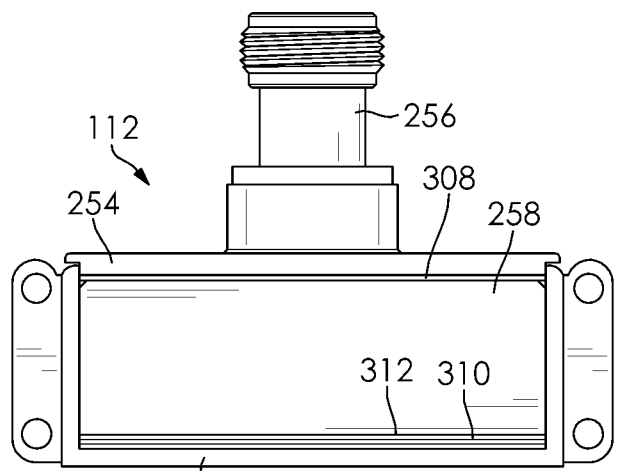
FIG. 8 shows a front view of an exemplary RF applicator with shims in more than one location, in accordance with some embodiments.

FIG. 8 shows a front view of an exemplary RF applicator 112 with shims 300 in another exemplary arrangement in the waveguide 250. As FIG. 8 shows, the compressible shim 308 may be disposed above the solid dielectric insert 258, while the conductive shim 310 and the first dielectric shim 312 are disposed below. In another embodiment, one or more additional dielectric shims are disposed therein.

The foregoing description, for purpose of explanation, has been described with reference to specific embodiments. However, the illustrative discussions above are not intended to be exhaustive or to limit the invention to the precise forms disclosed. Many modifications and variations are possible in view of the above teachings. The embodiments were chosen and described to best explain the principles of the techniques and their practical applications. Others skilled in the art are thereby enabled to best utilize the techniques and various embodiments with various modifications as are suited to the particular use contemplated.

Although the disclosure and examples have been fully described with reference to the accompanying drawings, it is to be noted that various changes and modifications will become apparent to those skilled in the art. Such changes and modifications are to be understood as being included within the scope of the disclosure and examples as defined by the claims.

We claim:

1. A radio frequency (RF) applicator, the RF applicator comprising:
   a waveguide having a first interior surface comprising a first aperture, a second interior surface opposing the first interior surface, a third interior surface adjacent to the first and second interior surfaces, a fourth interior surface opposing the third interior surface, and a fifth interior surface perpendicular to the first, second, third, and fourth interior surfaces;
   an aperture antenna;
   a solid dielectric insert within the waveguide, the solid dielectric insert having a second aperture formed therethrough that is configured for alignment with the first aperture;
   an RF connector, configured to receive generated RF energy pulses;
   at least one shim, wherein the at least one shim is planar-shaped and has a third aperture therethrough configured to align with the first and second apertures; and
   a radio frequency feed pin configured for electrical connection to the RF connector, wherein the radio frequency feed pin is disposed within the first, second, and third apertures and affixed to the second interior surface.

2. The radio frequency applicator of claim 1, wherein the aperture antenna comprises an opening defined by the first, second, third, and fourth interior surfaces of the waveguide, wherein the opening is perpendicular to the first, second, third, and fourth interior surfaces and opposing the fifth interior surface.

3. The radio frequency applicator of claim 2, further comprising:
   a conductive shim that is planar-shaped having a length corresponding to the fifth interior surface and the opening, and a width defined by the third and fourth interior surfaces and has a fourth aperture therethrough configured for alignment with the first and second apertures.

4. The radio frequency applicator of claim 3, wherein the conductive shim has a conductivity between $1 \times 10^6$ Siemens/meter and $1 \times 10^8$ Siemens/meter.

5. The radio frequency applicator of claim 1, further comprising:
   a compressible shim that is planar-shaped having a length corresponding to the fifth interior surface and the opening, and a width defined by the third and fourth interior surfaces and has a fourth aperture therethrough configured for alignment with the first and second apertures.

6. The radio frequency applicator of claim 5, wherein the compressible shim has a bulk modulus between 1.0 Mega Pascal and 1.0 Giga Pascal.

7. The radio frequency applicator of claim 5, wherein the compressible shim has an acoustic attenuation between 5 and 200 dB/(MHz*centimeter).

8. The radio frequency applicator of claim 1, wherein the solid dielectric insert comprises a length corresponding to the fifth interior surface and the opening, and a width defined by the third and fourth interior surfaces.

9. The radio frequency applicator of claim 8, wherein the solid dielectric insert has a real relative permittivity between about 20 and 180.

10. The radio frequency applicator of claim 1, wherein the at least one shim is a dielectric shim.

11. The radio frequency applicator of claim 1, wherein the at least one shim comprises a length corresponding to the fifth interior surface and the opening, and a width defined by the third and fourth interior surfaces.

12. The radio frequency applicator of claim 1, wherein the at least one shim has a real relative permittivity between about 20 and 180 and an imaginary relative permittivity between about 0 and 18.

13. A radio frequency (RF) applicator, the RF applicator comprising:
   a waveguide having a first interior surface comprising a first aperture, a second interior surface opposing the first interior surface, a third interior surface adjacent to the first and second interior surfaces, a fourth interior surface opposing the third interior surface, and a fifth interior surface perpendicular to the first, second, third, and fourth interior surfaces;
   an aperture antenna;
   a solid dielectric insert within the waveguide, the solid dielectric insert having a second aperture formed therethrough that is configured for alignment with the first aperture;
   an RF connector, configured to receive generated RF energy pulses;
   a plurality of planar-shaped shims, each having an aperture therethrough configured to align with the first and second apertures; and
   a radio frequency feed pin configured for electrical connection to the RF connector, wherein the radio frequency feed pin is disposed within the first, second, and third apertures and affixed to the second interior surface.

14. The radio frequency applicator of claim 13, wherein the plurality of planar-shaped shims comprises a conductive shim.

15. The radio frequency applicator of claim 14, wherein the conductive shim has a conductivity between $1 \times 10^6$ Siemens/meter and $1 \times 10^8$ Siemens/meter.

16. The radio frequency applicator of claim 13, wherein the plurality of planar-shaped shims comprises a compressible shim.

17. The radio frequency applicator of claim 16, wherein the compressible shim has a bulk modulus between 1.0 Mega Pascal and 1.0 Giga Pascal.

18. The radio frequency applicator of claim 16, wherein the compressible shim has an acoustic attenuation between 5 and 200 dB/(MHz*centimeter).

19. The radio frequency applicator of claim 13, wherein the plurality of planar-shaped shims comprises at least one dielectric shim.

20. The radio frequency applicator of claim 19, wherein dielectric shim has a real relative permittivity between about 20 and 180 and an imaginary relative permittivity between about 0 and 18.

21. A radio frequency (RF) applicator, the RF applicator comprising:
   a waveguide having a first interior surface comprising a first aperture, a second interior surface opposing the first interior surface, a third interior surface adjacent to the first and second interior surfaces, a fourth interior surface opposing the third interior surface, and a fifth interior surface perpendicular to the first, second, third, and fourth interior surfaces;

an aperture antenna;

a solid dielectric insert within the waveguide, the solid dielectric insert having a second aperture formed therethrough that is configured for alignment with the first aperture;

an RF connector, configured to receive generated RF energy pulses;

a plurality of planar-shaped shims, each having an aperture therethrough configured to align with the first and second apertures, wherein the plurality of planar-shaped shims comprises:
 a conductive shim,
 a compressible shim, and
 at least one dielectric shim; and a radio frequency feed pin configured for electrical connection to the RF connector, wherein the radio frequency feed pin is disposed within the first, second, and third apertures and affixed to the second interior surface.

22. The radio frequency applicator of claim 21, wherein the conductive shim has a conductivity between $1 \times 10^6$ Siemens/meter and $1 \times 10^8$ Siemens/meter.

23. The radio frequency applicator of claim 21, wherein the compressible shim has a bulk modulus between 1.0 Mega Pascal and 1.0 Giga Pascal.

24. The radio frequency applicator of claim 21, wherein the compressible shim has an acoustic attenuation between 5 and 200 dB/(MHz*centimeter).

25. The radio frequency applicator of claim 21, wherein dielectric shim has a real relative permittivity between about 20 and 180 and an imaginary relative permittivity between about 0 and 18.

26. The radio frequency applicator of claim 21, wherein the aperture antenna comprises an opening defined by the first, second, third, and fourth interior surfaces of the waveguide, wherein the opening is perpendicular to the first, second, third, and fourth interior surfaces and opposing the fifth interior surface.

27. The radio frequency applicator of claim 21, wherein the conductive shim, the compressible shim, and the at least one dielectric shim, are planar-shaped having a length corresponding to the fifth interior surface and the opening, and a width defined by the third and fourth interior surfaces and each have an aperture therethrough configured for alignment with the first and second apertures.

* * * * *